United States Patent [19]
Jammet

[11] Patent Number: 5,447,534
[45] Date of Patent: Sep. 5, 1995

[54] ELECTRODE FOR A HEART STIMULATING APPARATUS HAVING A RETRACTABLE BIOLOGICAL SCREW

[75] Inventor: Jean F. Jammet, Objat, France

[73] Assignee: Societe Etudes et Developpements-S.E.D., Objat, France

[21] Appl. No.: 128,678

[22] Filed: Sep. 30, 1993

[30] Foreign Application Priority Data

Oct. 1, 1992 [FR] France .................................. 92 11786

[51] Int. Cl.6 .............................................. A61N 1/05
[52] U.S. Cl. ................................................. 607/127
[58] Field of Search ............... 607/127, 116, 119, 131; 128/642

[56] References Cited

U.S. PATENT DOCUMENTS

| | | | |
|---|---|---|---|
| 4,217,913 | 8/1980 | Dutcher | 607/127 |
| 4,570,642 | 2/1986 | Kane et al. | 607/127 |
| 5,314,461 | 5/1994 | Borghi | 607/127 |

*Primary Examiner*—William E. Kamm
*Assistant Examiner*—Kennedy J. Schaetzle
*Attorney, Agent, or Firm*—Young & Thompson

[57] ABSTRACT

The electrode comprises a hollow body (10, 110), an inner mechanical screw (30, 130) cooperative with an internal screw thread (32, 132) provided inside the body, and a corkscrew member (66, 166) connected at one of its ends to the mechanical screw, the other end, of helical shape, being adapted to penetrate the fibrous tissues of the heart by rotation. The mechanical screw (30, 130) is provided with a groove (34, 134) disposed in the proximal part of the screw thread of the mechanical screw for defining a neutral position of the mechanical screw.

15 Claims, 5 Drawing Sheets

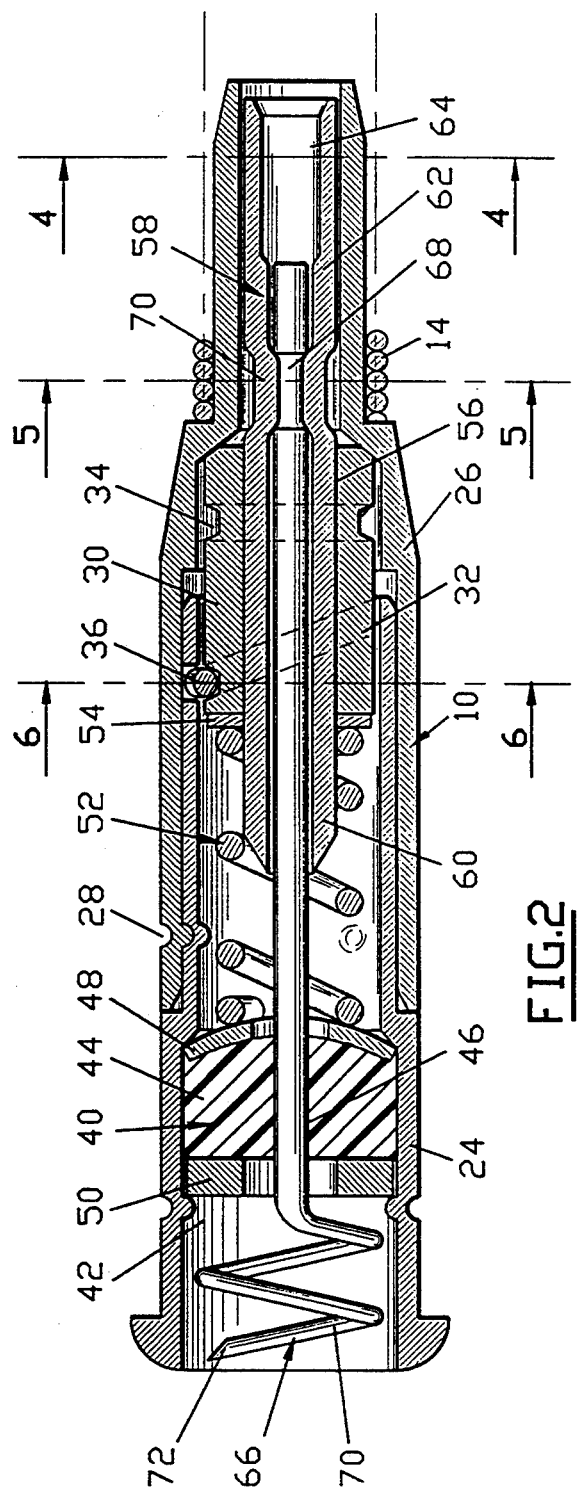
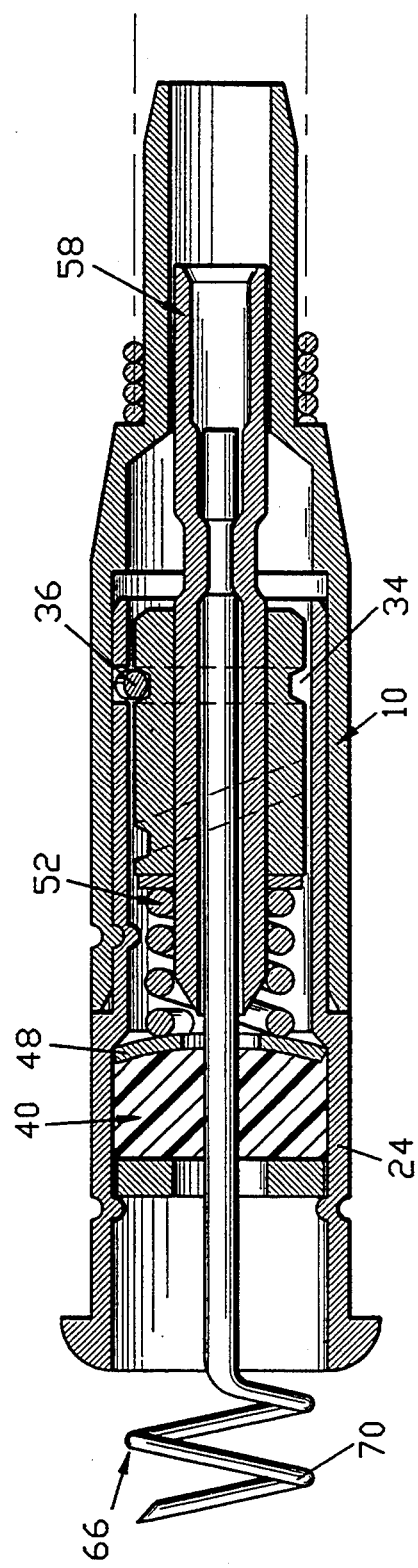
FIG.2
FIG.3

ELECTRODE FOR A HEART STIMULATING APPARATUS HAVING A RETRACTABLE BIOLOGICAL SCREW

The present invention relates to an electrode for a heart stimulating apparatus having a retractable biological screw.

Heart stimulating apparatuses comprise, in the known manner, an outer case provided with a source of energy and an electronic control system connected by means of a cable to an electrode which is fixed inside the heart, directly on the inner wall of one of the cavities concerned.

The problem is to introduce such an electrode through one of the vessels into the concerned cavity and then fasten this electrode to the wall, it being necessary to provide a sufficiently effective fastening to permit the transmission of electric signals.

Many devices have been developed and there is more particularly known that which is disclosed in the French patent FR-A-2 575 925 relating to a stimulating and detecting electrode for a heart probe.

For the purpose of achieving the anchorage of this electrode, a retractable biological screw is disposed in a cylindrical body constituting the electrode proper.

A flexible conductor cable connected to the body permits shifting this body constituting the electrode to within the concerned heart cavity, the biological screw being in the retracted position within the body throughout this travel.

The biological screw is in fact mounted on an element movable in translation inside the body, this movable element being a mechanical screw rotatively mounted in a tapping provided inside the body of the electrode.

The mechanical screw comprises in its upper part a blind bore for receiving an operating tool which is none other than a second cable which is provided with a terminal member adapted to cooperate with the blind bore of the screw and is freely movable coaxially inside the conductor cable.

This electrode operates and is employed in the following manner:

the electrode with the biological screw in the retracted position is introduced inside the vessel until it reaches the interior of the concerned cavity, when the free end of the electrode comes to bear against the wall of the cavity, the practitioner rotates the cable inside the conductor cable, and rotation of the mechanical screw through the conductor cable has for effect to move the anchoring biological screw in translation out of the body of the electrode.

When the electrode bears against the concerned wall, this biological screw, which has a sharp point, penetrates the fibrous tissue of the heart muscle.

It is then sufficient to connect the free end of the conductor cable to the stimulating apparatus proper.

The electrical contact with the tissues is good and this reduces the consumption of electricity required and results in more effective signal transmission.

In this patent FR-A-2 575 925, anchoring means are also provided in the form of flexible appendages arranged around the outer periphery of the body of the electrode.

While this type of assembly is fully satisfactory as concerns the quality of the anchoring and the quality of the electrical contact, there is nonetheless a problem concerning the utilization of this electrode.

Indeed, the practitioner must maintain the electrode pressed against the wall of the cavity before shifting the biological screw.

There are two possible situations, either the electrode is correctly in contact with the wall, and the biological screw, as it travels out of the body of the electrode, penetrates and becomes hooked in the tissue of the wall, or the electrode stops short of the wall of the cavity unbeknown to the practitioner.

In the latter case, the biological screw is rotated simultaneously with the mechanical screw and this causes the biological screw to project, but without becoming hooked in the wall.

The anchoring may be erroneously considered complete by the practitioner.

Further, the tactile sensitivity of the practitioner is handicapped by the fact that there is provided, between the biological screw and the free end of the actuating cable, an assembly comprising the mechanical screw and the tapping which does not transmit the reactions of the biological screw with fidelity.

Further, as the electrode has a diameter on the order of 3 mm, it is difficult to finely control the torque when using the arrangement just described.

Bearing in mind the necessarily very small overall size of the electrode, the mechanical screw is short and this makes it necessary, in the event that the electrode is not anchored, to rotate the actuating cable in the opposite direction to cause the mechanical screw to move rearwardly and once more have available a sufficient travel to permit the full penetration of the biological screw when it is subsequently made to project.

Therefore, the present invention overcomes this drawback by providing an electrode having a retractable biological screw which enables the practitioner to "feel" the hooking and anchoring of the biological screw in the wall of the cavity, this electrode also permitting rotating the biological screw until it penetrates the wall with no limitation of the number of rotations and rotating in a single direction until the anchorage has been achieved.

An alternative embodiment of the invention also provides for the rotation of the body of the screw.

The electrode according to the invention may also be withdrawn by a reverse rotation whenever required.

Furthermore, this electrode, apart from providing an excellent electrical contact, avoids any deterioration of the mechanical part by entry of liquid inside the electrode, owing to the provision of a highly effective fixed seal around the biological screw.

For this purpose, the electrode according to the invention, of the type having a retractable biological screw and intended for a heart stimulating apparatus, comprises a body provided with an internal screw thread, an inner mechanical screw cooperative with said screw thread, and a biological screw connected at one of its ends to the mechanical screw, the other end, of helical shape, being provided for penetrating the fibrous tissues of the heart by rotation, and this electrode is characterized in that the mechanical screw is provided with a "neutral position" groove disposed in the proximal part of the screw thread.

This electrode is also characterized in that it comprises a fixed seal mounted in the distal part of the body and clamped in the latter by thrust means employing a washer.

According to another characteristic, the thrust means comprise a proximal second washer bearing against a counterbore in the body of the electrode which receives one of the ends of a return spring interposed between the mechanical screw and this washer.

In an alternative embodiment, the thrust means comprise a first washer fixed with respect to the body immediately on the proximal side of the seal, a second washer bearing against the proximal end of the seal, and a second spring, coaxial with the first-mentioned spring, extending through the first washer and bearing against the second washer, the two springs bearing by their opposite ends against the mechanical screw.

In a preferred embodiment of the invention, the mechanical screw comprises a coaxial inner sleeve projecting from the proximal end of the mechanical screw, the downstream end of the sleeve, or an extension of the mechanical screw, permitting a centering of the spring or springs, while the proximal part of the sleeve is adapted to cooperate with an actuating tool.

According to a particular feature, the proximal end of the biological screw is held fast inside the sleeve by the provision of flat portions on the sleeve and biological screw.

Likewise, the free proximal end of the sleeve adapted to receive the free end of the actuating tool, is also flattened.

A conductor cable of the type having contacting coils is connected to the proximal end of the body of the electrode, the assembly comprising the body and the cable being protected externally by a sheath.

In a particular embodiment, the mechanical screw is provided with a screw thread which is cooperative with a fixed projecting lug inside the body of the electrode.

This lug is in fact an inclined pin disposed substantially along a chord of the inner cylindrical cavity of the body of the electrode.

In an alternative embodiment, this lug is formed by a deformation of the body of the electrode.

A particular embodiment and an alternative embodiment of the invention is described hereinafter with reference to the accompanying drawings in which:

FIG. 2 is a longitudinal sectional view of the electrode according to the invention;

FIG. 3 is a longitudinal sectional view of the electrode according to the invention with the biological screw projecting;

Figure 1:
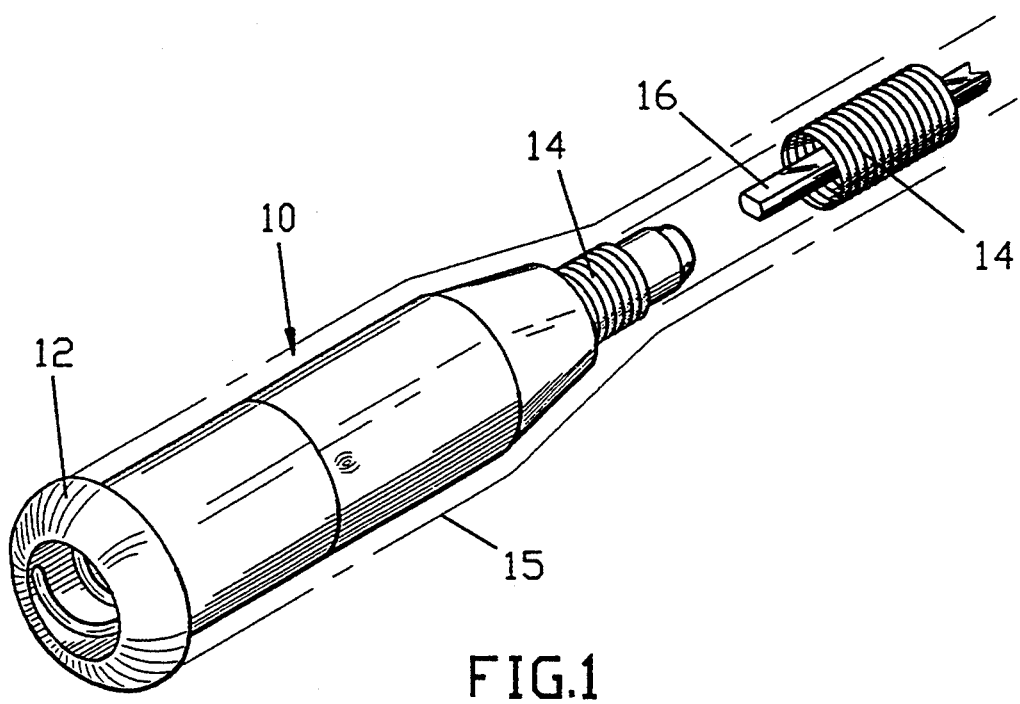
FIG. 1 is a perspective view of the electrode according to the invention and of portions of the conductor cable and actuating cable.

In FIG. 1, there is shown the body 10 of the electrode provided with a lip 12 of rounded shape at its distal end, and a conductor cable 14 connected to its proximal end and covered with a continuous sheath 15.

This conductor cable 14 is connected in the known manner to the heart stimulating apparatus proper (not shown).

Partly shown in FIG. 1 is the actuating cable 16 provided with flat faces.

The distal end of the electrode is open and there can be seen the sharp pointed end of the last coil of the biological screw which is shown in its retracted position and will be described in detail hereinafter.

In FIG. 2, the body 10 of the electrode is made in two parts, namely a part 24 forming the distal semi-body and a part 26 forming the proximal semi-body, these two semi-bodies being mechanically interconnected by indentations 28 arranged 120° apart in the illustrated embodiment.

The conductor cable 14 having contacting coils is disposed at the free end of the proximal semi-body 26.

Provided inside the body 10 of the electrode is a mechanical screw 30 provided with a screw thread 32 and a "neutral position" groove 34 located on the proximal side of the screw thread 32.

This screw thread and this groove are adapted to cooperate with a lug 36 projecting inside the body 10 of the electrode.

Figure 6:
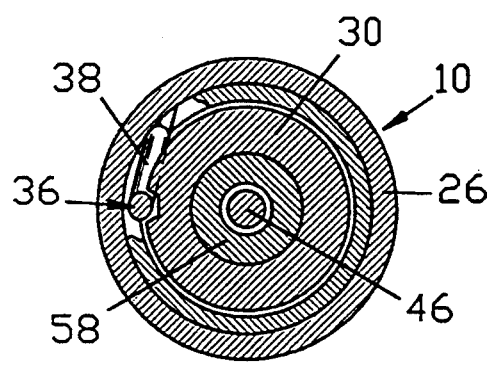

This lug 36 is seen better in FIG. 6 and consists of a cylindrical pin 38 which is inclined and disposed along a chord of the cylindrical inner cavity of the body of the electrode.

The electrode further comprises a fixed seal 40 disposed in a counterbore 42 provided inside the body of the electrode adjacent to the distal part.

The seal 40 comprises a ring 44 of elastomer provided with a bore 46 produced without removing material and centered on the longitudinal axis of the body of the electrode, a proximal washer 48 and a distal washer 50. The washer 50 is mounted in the counterbore 42 so as to block the ring 44 and is held in position by the deformation of the wall produced by indentations, while the washer 48, which abuts against the inner end of the counterbore, clamps the elastomer ring in position.

Further, as is shown, this washer is slightly curved in the proximal direction under the effect of the compression of the seal against the washer 50.

Interposed between the mechanical screw 30 and the washer 48 is a spring 52 whose proximal end bears against a washer 54 placed flat against the distal end of the mechanical screw 30.

The mechanical screw 30 further comprises a central bore 56 in which a sleeve 58 is a drive fit.

The sleeve projects from the distal end of the screw by a portion 60 and the compressed spring 52 acts as a thrust member.

The sleeve 58 also projects at the proximal end by a proximal portion 62. This proximal portion of the sleeve defines a counterbore 64 which is open at the proximal end.

The electrode according to the invention shown in FIG. 2 further comprises a biological screw 66 provided at its proximal end with a narrowed portion 68 locked in a flattened portion 70 of the sleeve 58 and having at its distal end a coil 70 whose free end 72 has a sharp point.

In FIG. 2, the biological screw is in the retracted position and the axial portion extends through the sleeve 58, the spring 52, the distal washer 48, the elastomer ring 44 and the locking washer 50, the coil 70 being fully contained in the counterbore 42.

In FIG. 3, which is a view in which the references concerning identical elements are retained, the mechanical screw 30 is in a displaced position which is such that the lug 36 is located in the "neutral position" groove 34, the spring 52 is in the compressed position, the washer 48 is slightly flattened and the coil 70 projects out of the body of the electrode.

Figure 4:
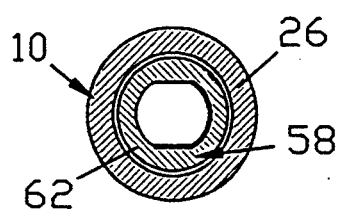
FIGS. 4, 5 and 6 are cross-sectional views respectively taken on lines 4—4, 5—5, 6—6 of FIG. 2.
Figure 5:
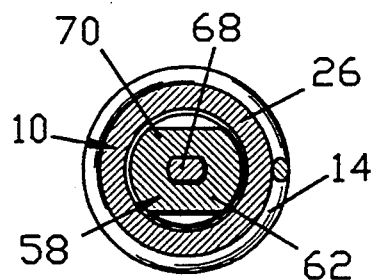

FIGS. 4 and 5 are cross-sectional views and identical elements carry the same reference characters as those in FIGS. 2 and 3.

A detailed description of the operation and the utilization of the electrode just described will now be given.

Figure 7:
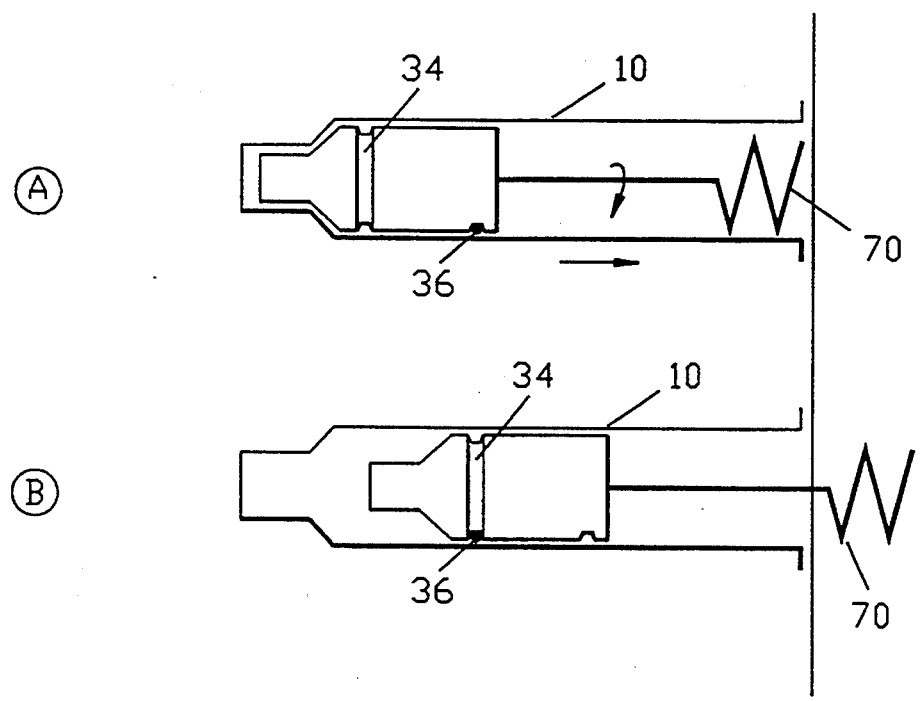
FIG. 7 represents a first diagram of the utilization of the electrode according to the invention.

The electrode according to the invention is placed in position by the practitioner by inserting in one of the vessels the body of the electrode 10 and by pushing it by means of the conductor cable 14 until it reaches the interior of the concerned heart cavity as shown in FIGS. 7A and 7B.

When the practitioner esteems, with the aid of his medical supervising means, that the electrode is in contact with the wall in which it must be anchored, he introduces the actuating cable 16 in the conductor cable 14 until it enters the counterbore 64, the biological screw 66 being in the retracted position.

He can now move this cable 16 in translation with no risk of displacing the biological screw.

It is then sufficient for the practitioner to rotate the actuating cable to drive in rotation the mechanical screw 30 which is connected to the sleeve 58, and cause the screw thread 32 to cooperate with the lug 36 which is fixed with respect to the body of the electrode.

The rotation of the mechanical screw 30 causes it to travel inside the body of the electrode until the lug 36 cooperates with the "neutral position" groove 34.

The biological screw of the electrode is thereby made to project from the electrode in the position shown in FIG. 3.

As the electrode is in contact with the inner wall of the concerned cavity of the heart, the biological screw penetrates the fibrous tissue under the action of its sharp point.

The practitioner rotates the actuating cable until he feels a resistance which indicates a good anchoring of the biological screw. The transmission of the resisting torque is very good, since it is direct.

The number of rotations is unlimited, since the mechanical screw cooperates with the projecting lug 36 through the medium of its "neutral position" groove which allows rotation without causing an axial displacement.

The biological screw and the electrode are in the position shown in FIG. 7B, the vertical line representing the wall of the fibrous tissue.

In some cases, the practitioner may wrongly esteem that the electrode is in contact with the wall of the cavity, for example owing to lack of precision of the supervising and display means.

Figure 8:
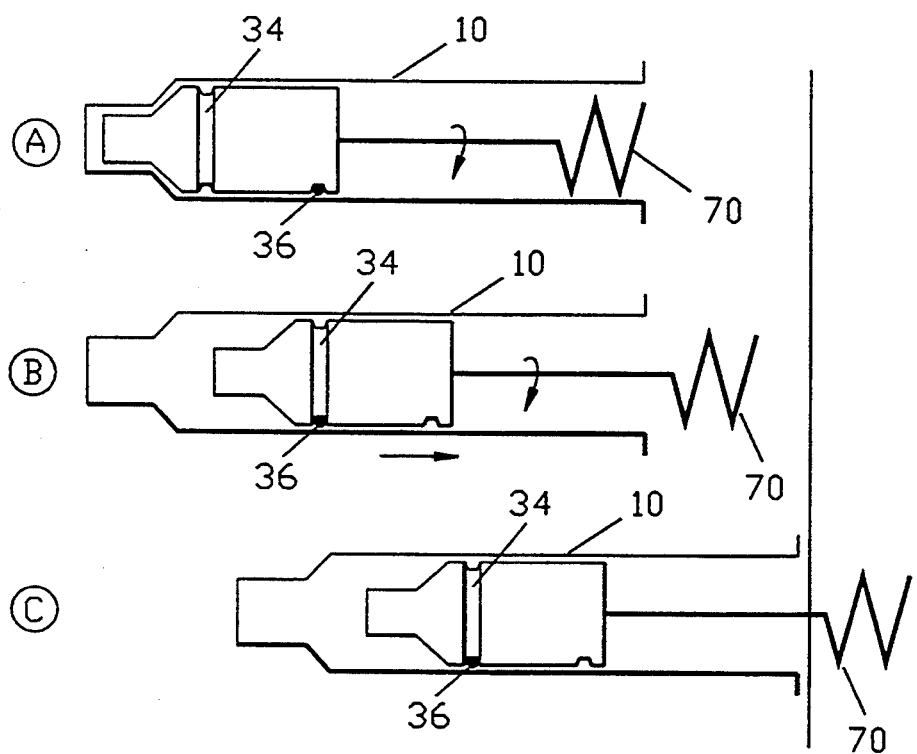
FIG. 8 represents a second diagram of the utilization of the electrode according to the invention.

In this case, the electrode is in the position shown in FIG. 8A, i.e. the biological screw is retracted and the distal end of the electrode is slightly spaced away from the wall of the cavity.

As mentioned before, the practitioner inserts the actuating cable and causes the biological screw to project, with the electrode in the position shown in FIG. 8B.

As can be seen, the biological screw has rotated in space and not entered the fibrous tissue of the cavity.

Further, the practitioner does not "feel" any resistant torque notwithstanding the fact that the screw was rotated through several rotations. Informed of this fact directly by the handling, it is then sufficient for him to cause an additional movement of translation of the conductor cable to advance the electrode while causing the biological screw to effect rotations by means of the actuating cable.

The electrode approaches the wall of the cavity until the biological screw "bites" into the fibrous tissue. The practitioner will encounter a resistance as soon as the distal end of the body of the electrode comes to bear against the fibrous tissue and the biological screw has completely penetrated the latter. The anchorage is then complete.

The electrode according to the invention has therefore this important advantage of permitting an anchorage in a single simple operation even when the body of the electrode is not in direct contact with the wall on which it must be placed.

The handling is simple and the number of parts making up the electrode is small, which renders it all the more reliable.

As concerns the electrical quality of the contacts, it is good bearing in mind the fact that the sealing action of the fixed seal around the biological screw is enhanced when this biological screw is moved in translation, since the spring exerts a pressure on the proximal washer 48 which compresses the ring 44 of elastomer around this biological screw, and any deterioration of the conductor components is avoided.

Further, the seal has a diameter slightly larger than that of the counterbore 42 so as to improve the sealing action in the manner of a bottle stopper.

The spring also has another function which is to exert a permanent force on the mechanical screw, so that the electrode according to the invention may be easily withdrawn by reverse rotation of the actuating cable which drives the mechanical screw in reverse rotation since, as soon as the projecting lug 36 crosses the screw thread it engages in the latter.

Figure 9:
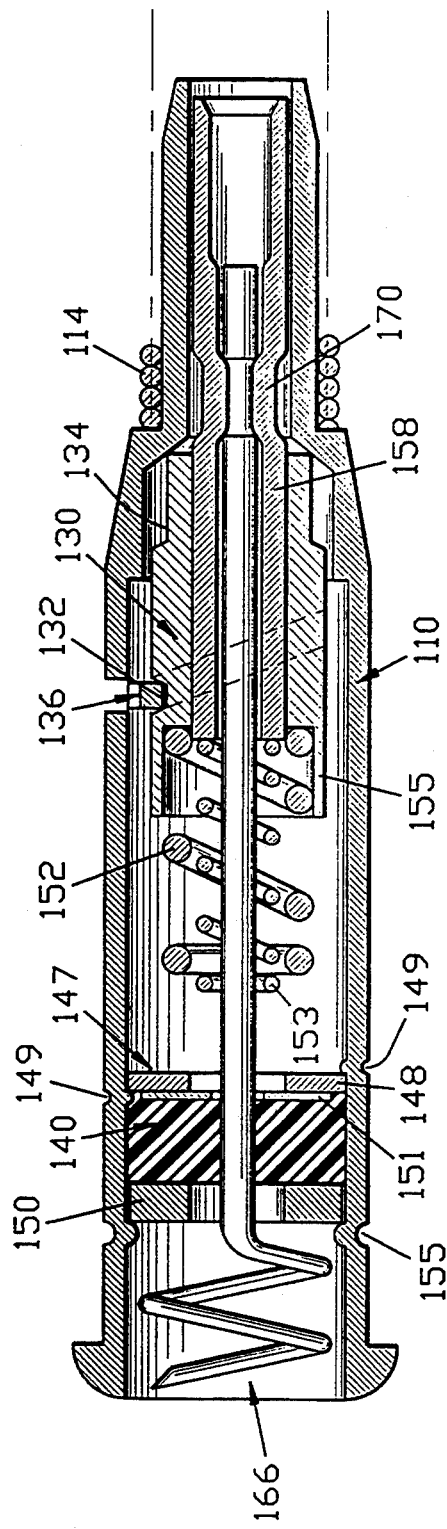
FIG. 9 is a view of an alternative embodiment of the electrode and more particularly of the means for exerting a thrust on the seal and the lug for the mechanical screw.
Figure 10:
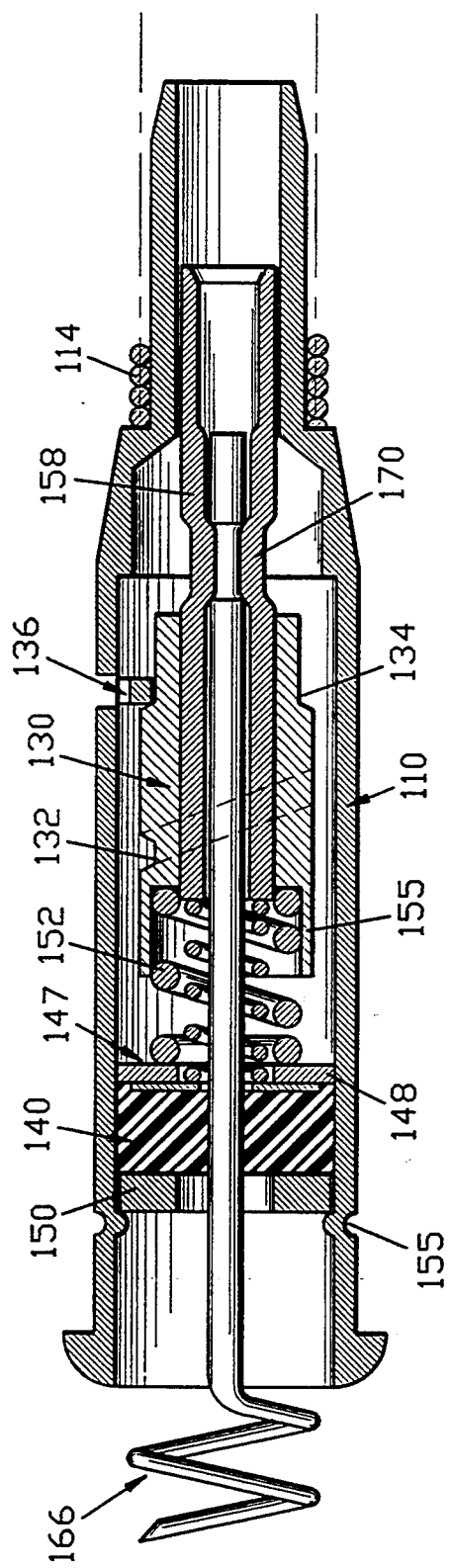
FIG. 10 is a view identical to FIG. 9 with the biological screw projecting.

FIGS. 9 and 10 show another embodiment the utilization of which may be preferred by practitioners.

Identical reference characters in FIGS. 2 and 3 are the same increased by 100 for FIGS. 9 and 10.

This embodiment comprises a single body 110 in which is mounted a mechanical screw 130 to which is connected a biological screw 166 through the medium of a sleeve 158.

A fixed washer 150 is blocked in position with respect to the body 110 by deformations 155 evenly spaced apart on the periphery.

A seal 140, disposed on the upstream side of this washer bears against the latter and, on the periphery, against the interior of the body 110.

On the proximal side of the seal, thrust means 147 are provided which comprise a first washer 148 fixed relative to the body owing to the provision of deformations 149, and a second washer 151 freely disposed between the distal end of the seal and the first washer.

The fixed washer 150, the seal 140 and the first and second washers 148 and 151 of the thrust means are provided with a central bore through which the biological screw extends.

The bore, formed without removal of material, through the seal 140 closely fits the body of the biological screw.

The central bore of the first washer has a diameter larger than that of the bore of the second washer.

The thrust means also include a spring 153 connected to the mechanical screw 130 and having such length that it exerts at rest, i.e. when the mechanical screw is in the withdrawn position, no force on the second free washer 151.

The spring 153 has a diameter between the diameters of the first and second washers 148 and 151. The mechanical screw 130 includes, in the same way as in the main embodiment, a return spring 152.

The two springs 152 and 153 are coaxial and guided by a skirt 155 extending the distal end of the mechanical screw 130.

The mechanical screw 130 is unchanged and includes a screw thread 132 and a "neutral position" groove 134.

The lug 136 is produced by a deformation of a portion of the body of the electrode: two transverse cuts on a portion of an arc define a strip which is deformed inwardly of the body so as to project inside the body and form the lug.

The groove may also be open at the proximal end as shown in FIGS. 9 and 10.

The lug has such dimensions as to be cooperative with the screw thread 132.

The other elements of the electrode are unchanged.

The biological screw is fixed to the mechanical screw by a narrowed portion 170 and the conductor cable 114 remains connected to the proximal end of the body 110.

The operation and utilization of this alternative embodiment are slightly different from those of the preceding electrode.

Indeed, the electrode is brought in the same way into the concerned cavity of the heart.

Figure 11:
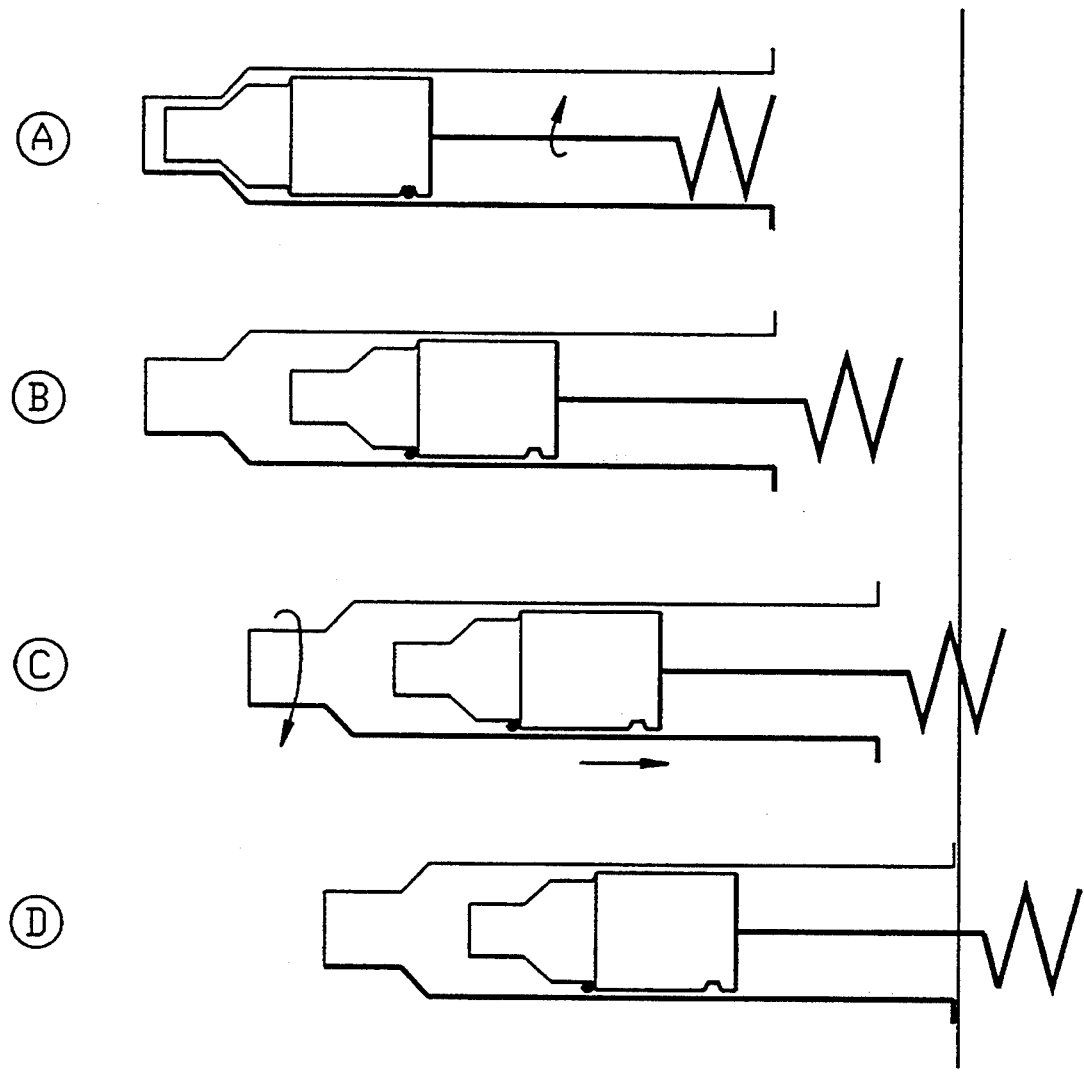
FIG. 11 represents the diagram of the utilization of this alternative embodiment.

It is in stage A of FIG. 11, that an actuating cable provided for cooperation in rotation with the mechanical screw, causes by the action of rotation on the part of the practitioner, the biological screw to project, the body being maintained fixed in rotation.

In an alternative embodiment, the actuating cable may remain fixed and the practitioner may rotate the body of the electrode, the result being identical, namely the projection of the biological screw.

It will be observed that this stage occurs before the body comes into contact with the wall of the cavity. During the stage B, the practitioner withdraws the first actuating cable and replaces it with a second actuating cable having a rounded end which precludes any action of rotation on the mechanical screw.

This actuating cable, bent by the practitioner, allows the electrode to be placed in position in regions to which access is more difficult.

The practitioner then pushes on the body of the electrode with the actuating cable which bears against the mechanical screw, while turning the body 110 of the electrode.

Frictional forces, created by the screw in the seal, the springs and the mechanical screw engaged with the lug, are sufficient to ensure the penetration by screwing of the biological screw into the heart tissue.

In stage C, the biological screw penetrates the tissue.

When the biological screw is fully screwed in, the practitioner is informed that he can stop when he feels the rotation of the body relative to the mechanical screw.

Indeed, the frictional forces are insufficient relative to the force exerted by the practitioner, since the biological screw is prevented from rotating in the tissue.

The "neutral position" groove precludes any relative displacement between the body and the mechanical screw and the practitioner feels a "click" when the lug "jumps" the screw thread so as to remain in the "neutral position" groove. This is stage D.

During all these stages, and as soon as the biological screw projects, the spring 153, extending through the first washer 148, exerts its force on the second washer 151 under the thrust exerted by the mechanical screw 130.

The fixed washer 150 permits the second washer 151 to compress the seal 140, which improves the primary sealing action due to an increase in size of the seal around the biological screw and on the inner wall of the body 110.

The continuous outer sheath 15 which covers the whole of the body and the conductor cable, provides a peripheral seal.

The conductor cable is connected in the known manner to the stimulating apparatus proper.

I claim:

1. Electrode for a heart stimulating apparatus comprising in combination: a retractable corkscrew member, a hollow body, an internal screw thread inside the body, a inner mechanical screw having a screw thread cooperative with said internal screw thread, said corkscrew member having one end connected to said mechanical screw and an opposite end which has a helical shape adapted to penetrate the fibrous tissues of the heart by rotation of said corkscrew member, said mechanical screw having a groove located adjacent the proximal end of said screw thread of said mechanical screw for defining a neutral position of the mechanical screw.

2. Electrode according to claim 1, comprising a fixed seal which includes a ring composed of elastomer mounted in a distal part of said body of said electrode, and a washer for clamping said seal in said body.

3. Electrode according to claim 1, wherein there is a counterbore in said body of said electrode and said seal comprises at the proximal end thereof washer means bearing against an end of said counterbore.

4. Electrode according to claim 3, comprising spring means between the distal end of said mechanical screw and said washer means disposed proximally of said fixed seal.

5. Electrode according to claim 4, wherein said washer means comprise two washers and said spring means comprise two springs.

6. Electrode according to claim 4, wherein said electrode has an actuating cable and said mechanical screw comprises an inner coaxial sleeve which projects from the proximal end of said mechanical screw, said sleeve having a distal end engaged with said spring means for centering said spring means, and a proximal end adapted to receive and cooperate with an end of said actuating cable.

7. Electrode according to claim 4, wherein said electrode has an actuating cable and said mechanical screw comprises an inner coaxial sleeve which projects from the proximal end of said mechanical screw, an extension of said mechanical screw being engaged with said spring means for centering said spring means, and said sleeve having a proximal end adapted to receive and cooperate with an end of said actuating cable.

8. Electrode according to claim 6, wherein said sleeve has a flattening thereon and said corkscrew member comprises a narrowed portion for locking said corkscrew member inside said sleeve by cooperation with said flattening of said sleeve.

9. Electrode according to claim 7, wherein said sleeve has a flattening thereon and said corkscrew member comprises a narrowed portion for locking said corkscrew member inside said sleeve by cooperation with said flattening of said sleeve.

10. Electrode according to claim 6, wherein the proximal end of said sleeve adapted to receive said end of said actuating cable is flattened.

11. Electrode according to claim 7, wherein the free proximal end of said sleeve adapted to receive said end of said actuating cable is flattened.

12. Electrode according to claim 1, wherein a conductor cable comprising a spring having closely wound touching coils is connected to the proximal end of said body of said electrode.

13. Electrode according to claim 1, wherein said screw thread of said mechanical screw is cooperative with a projecting lug inside said body of said electrode which constitutes said internal screw thread.

14. Electrode according to claim 13, wherein said lug is an inclined pin disposed substantially along a chord of a cylindrical inner cavity of said body of said electrode.

15. Electrode according to claim 13, wherein said lug is a deformation of said body of said electrode.

* * * * *